(12) United States Patent
Larson

(10) Patent No.: US 10,524,883 B2
(45) Date of Patent: Jan. 7, 2020

(54) ORTHODONTIC BRACKET

(71) Applicant: Robert G. Larson, Carmel, IN (US)

(72) Inventor: Robert G. Larson, Carmel, IN (US)

( * ) Notice: Subject to any disclaimer, the term of this patent is extended or adjusted under 35 U.S.C. 154(b) by 0 days.

(21) Appl. No.: 15/805,795

(22) Filed: Nov. 7, 2017

(65) Prior Publication Data

US 2018/0125611 A1 May 10, 2018

Related U.S. Application Data

(60) Provisional application No. 62/419,417, filed on Nov. 8, 2016.

(51) Int. Cl.
*A61C 7/14* (2006.01)
*A61C 7/30* (2006.01)

(52) U.S. Cl.
CPC .............. *A61C 7/14* (2013.01); *A61C 7/303* (2013.01)

(58) Field of Classification Search
CPC .............. A61C 7/14; A61C 7/12; A61C 7/30
See application file for complete search history.

(56) References Cited

U.S. PATENT DOCUMENTS

| | | | |
|---|---|---|---|
| 3,423,833 A * | 1/1969 | Pearlman | A61C 7/12 433/15 |
| 3,464,112 A | 9/1969 | Silverman | |
| 3,721,005 A * | 3/1973 | Cohen | A61C 7/14 433/16 |
| 3,765,091 A | 10/1973 | Northcutt | |
| 3,959,880 A * | 6/1976 | Andrews | A61C 7/12 433/11 |
| 4,077,126 A | 3/1978 | Pletcher | |
| 4,139,945 A * | 2/1979 | DiGiulio | A61C 7/12 433/16 |
| 4,337,037 A | 6/1982 | Kurz | |
| 4,531,911 A | 7/1985 | Creekmore | |
| 4,597,739 A * | 7/1986 | Rosenberg | A61C 7/14 433/16 |
| 4,614,497 A | 9/1986 | Kurz | |
| 4,659,309 A | 4/1987 | Merkel | |
| 4,867,678 A | 9/1989 | Parker | |
| 4,877,398 A | 10/1989 | Kesling | |
| 4,900,251 A | 2/1990 | Anreasen | |
| 4,927,360 A | 5/1990 | Pospisil | |
| 5,125,831 A | 6/1992 | Pospisil | |
| 5,161,969 A | 11/1992 | Pospisil | |
| 5,248,257 A | 9/1993 | Cannon | |
| 5,299,934 A * | 4/1994 | Suyama | A61C 7/12 433/10 |
| 5,320,525 A | 6/1994 | Forster | |
| 5,358,402 A | 10/1994 | Reed | |
| 5,380,196 A | 1/1995 | Kelly | |
| 5,380,197 A | 1/1995 | Hanson | |
| 5,542,842 A | 8/1996 | Andreiko | |

(Continued)

*Primary Examiner* — Ralph A Lewis
(74) *Attorney, Agent, or Firm* — Barnes & Thornburg LLP

(57) ABSTRACT

An orthodontic bracket assembly includes a mounting plate configured to be coupled to a tooth and a bracket member. The bracket member has a first portion generally extending in a first direction, a second portion generally extending in a second direction opposite to the first direction, and a slot defined intermediate the first and second portions. The slot is configured to receive a wire. Additionally, each of the first and second portions includes a curved surface defining an entrance of the slot.

14 Claims, 15 Drawing Sheets

(56) References Cited

U.S. PATENT DOCUMENTS

| | | | |
|---|---|---|---|
| 5,597,302 | A | 1/1997 | Pospisil |
| 5,618,175 | A * | 4/1997 | Reher .................... A61C 7/141 433/16 |
| 5,630,716 | A | 5/1997 | Hanson |
| 5,746,592 | A | 5/1998 | Nezu |
| 5,827,058 | A | 10/1998 | Kelly |
| 5,857,849 | A | 1/1999 | Kurz |
| 6,071,119 | A | 6/2000 | Christoff |
| 6,193,350 | B1 | 2/2001 | Hadley |
| 6,361,314 | B1 | 3/2002 | Garton |
| 6,478,579 | B1 | 11/2002 | Brusse |
| 6,554,612 | B2 | 4/2003 | Georgakis |
| 6,709,268 | B2 | 3/2004 | Pospisil |
| 7,140,875 | B2 | 11/2006 | Lai |
| 7,214,057 | B2 | 5/2007 | Voudouris |
| 7,306,458 | B1 * | 12/2007 | Lu ............................ A61C 7/14 433/16 |
| 7,431,586 | B1 * | 10/2008 | Silverman ................ A61C 7/14 433/9 |
| 7,621,743 | B2 | 11/2009 | Bathen |
| 7,963,768 | B2 | 6/2011 | Hilliard |
| 9,198,740 | B2 * | 12/2015 | Damon .................... A61C 7/14 |
| 9,408,676 | B2 * | 8/2016 | Rahimi .................... A61C 7/14 |
| 9,949,806 | B2 * | 4/2018 | Cosse .................... A61C 7/285 |
| 2006/0014116 | A1 | 1/2006 | Maijer |
| 2007/0166658 | A1 | 7/2007 | Voudouris |
| 2010/0178629 | A1 | 7/2010 | Oda |

* cited by examiner

ORTHODONTIC BRACKET

CROSS-REFERENCE TO RELATED APPLICATIONS

The present application claims priority to U.S. Provisional Patent Application Ser. No. 62/419,417, filed Nov. 8, 2016, and entitled "ORTHODONTIC BRACKET," the complete disclosure of which is expressly incorporated by reference herein.

FIELD OF THE DISCLOSURE

The present disclosure generally relates to structures for implementing orthodontia treatments. The present disclosure relates more specifically to an orthodontic bracket assembly configured to facilitate insertion of a wire thereon.

BACKGROUND OF THE DISCLOSURE

Orthodontic brackets are adhered to teeth. Each bracket has a slot therein that receives a wire which extends between multiple teeth. The wire is used to exert force on the teeth to obtain movement thereof. The upper and lower walls of the slot are typically parallel and straight along their entire depth.

The parallel walls may make it difficult to place the wire into the slot, especially when the width of the wire is very close to the width of the slot, which is often the case. For example, when the parallel walls defining the slot have linear surfaces at the entrance of the slot, it can be difficult to insert the wire therein. Additionally, the configuration of such a bracket only allows for adjustment of the teeth through the force of the wire against the bracket, however, there is no ability to rotate or adjust the position of a portion of the bracket with conventional orthodontic brackets.

Therefore, there is a need for an orthodontic bracket which allows for easier insertion and/or positioning of a wire within the slot of the bracket and also for a bracket which may allow for additional adjustment(s) on the tooth.

SUMMARY OF THE DISCLOSURE

In one embodiment of the present disclosure, an orthodontic bracket assembly comprises a mounting plate configured to be coupled to a tooth and a bracket member. The bracket member has a first portion generally extending in a first direction, a second portion generally extending in a second direction opposite to the first direction, and a slot defined intermediate the first and second portions. The slot is configured to receive a wire. Additionally, each of the first and second portions includes a curved surface defining an entrance of the slot.

In another embodiment of the present disclosure, an orthodontic bracket assembly comprises a first member configured to couple with a tooth and a second member configured to be removably coupled to the first member. The second member is configured to be in contact with a portion of a wire applied to the orthodontic bracket.

In a further embodiment of the present disclosure, an orthodontic bracket assembly comprises a mounting plate configured to be coupled with a tooth and a bracket member. The bracket member has a slot configured to receive a wire. Additionally, the slot is configured to move between a plurality of discrete positions relative to the mounting plate.

Additional features and advantages of the present invention will become apparent to those skilled in the art upon consideration of the following detailed description of the illustrative embodiment exemplifying the best mode of carrying out the invention as presently perceived.

BRIEF DESCRIPTION OF THE DRAWINGS

The detailed description of the drawings particularly refers to the accompanying figures in which.

DETAILED DESCRIPTION OF THE DISCLOSURE

The embodiments of the invention described herein are not intended to be exhaustive or to limit the invention to precise forms disclosed. Rather, the embodiments selected for description have been chosen to enable one skilled in the art to practice the invention. Although the disclosure is described in connection with water, it should be understood that additional types of fluids may be used.

Referring to FIGS. 1-5, an orthodontic bracket assembly 10 is shown. Bracket assembly 10 includes a mounting base or plate 12, a support member 14, and a bracket member 16. Mounting plate 12 is configured to be attached a tooth using convention adhesive or bonding materials and processes. In this way, mounting plate 12 remains in a fixed position on the tooth unless removed therefrom and reattached. Mounting plate 12 may be comprised of a ceramic material, although additional embodiments of mounting plate 12 may be comprised of polymeric and/or metallic materials instead of or in addition to a ceramic material. In one embodiment, mounting plate 12 may be configured in an octagonal shape, however, mounting plate 12 may be formed in any shape necessary for attaching to the tooth and/or the application of the orthodontic treatment. Illustrative mounting plate 12 also includes rounded or curved edges along a perimeter thereof, which may define a reduction in the amount of mounting plate 12 which is visible, thereby improving the aesthetics of bracket assembly 10 on a patient's tooth.

Figure 5:
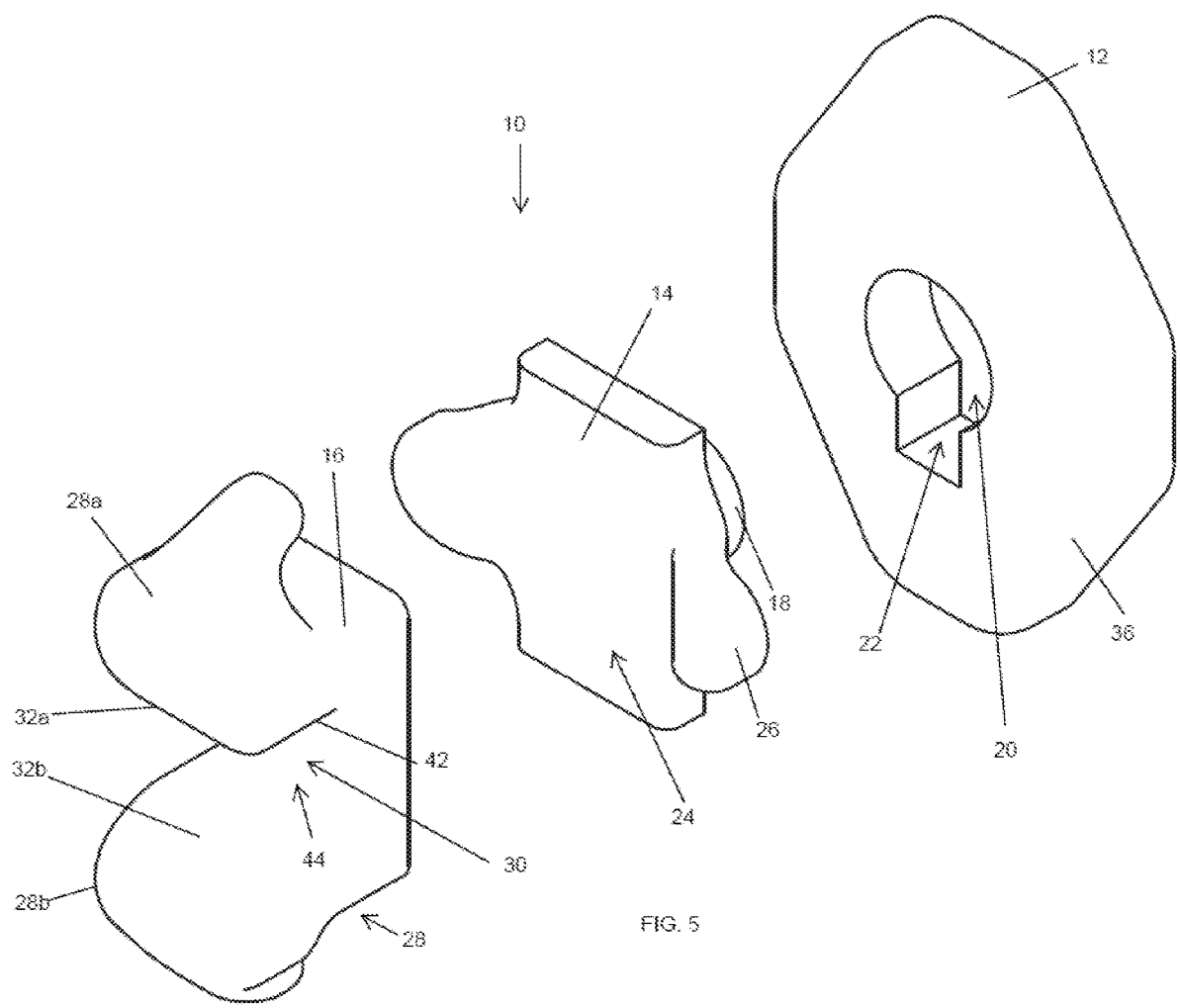
FIG. 5 is an exploded view of the bracket assembly of FIG. 1.

Referring still to FIGS. 1-5, in one embodiment, support member 14 is integrally formed with mounting plate 12, however, as shown in FIG. 5, support member 14 may be removably coupled to mounting plate 12. As shown best in FIG. 5, if support member 14 is configured to be removably coupled to mounting plate 12, support member 14 includes a protrusion 18 extending rearwardly (i.e., towards a tooth) therefrom. Protrusion 18 is configured to be received within an opening 20 of mounting plate 12. When support member 14 is coupled to mounting plate 12, additional coupling members (e.g., mechanical fasteners, adhesive, welds, bonds, or any other type of coupling mechanism) may be used to secure support member 14 to mounting plate 12. In one embodiment, protrusion 18 and opening 20 may be configured with a locking feature, such as a key or other projection on protrusion 18 (not shown) configured to be received within a slotted portion 22 of opening 20. Rotational movement or other techniques may be used to then secure support member 14 to mounting plate 12 through the key (not shown) on protrusion 18 and opening 20.

Figure 2:
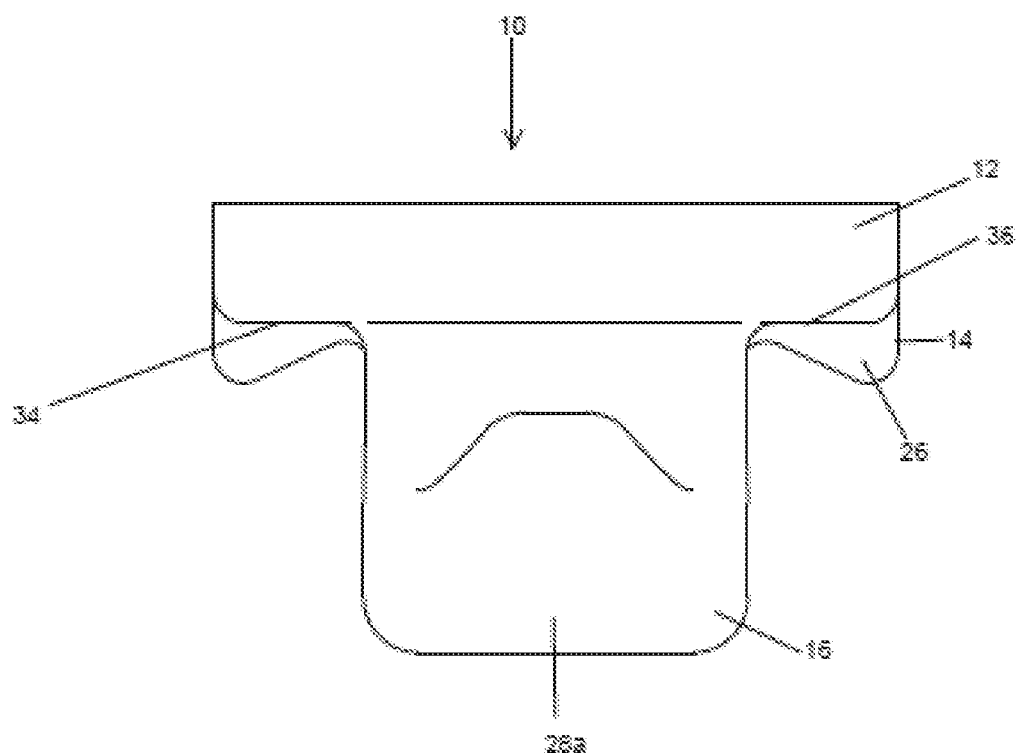
FIG. 2 is a top view of the bracket assembly of FIG. 1, where a bottom view of the bracket assembly of FIG. 1 is identical.
Figure 3:
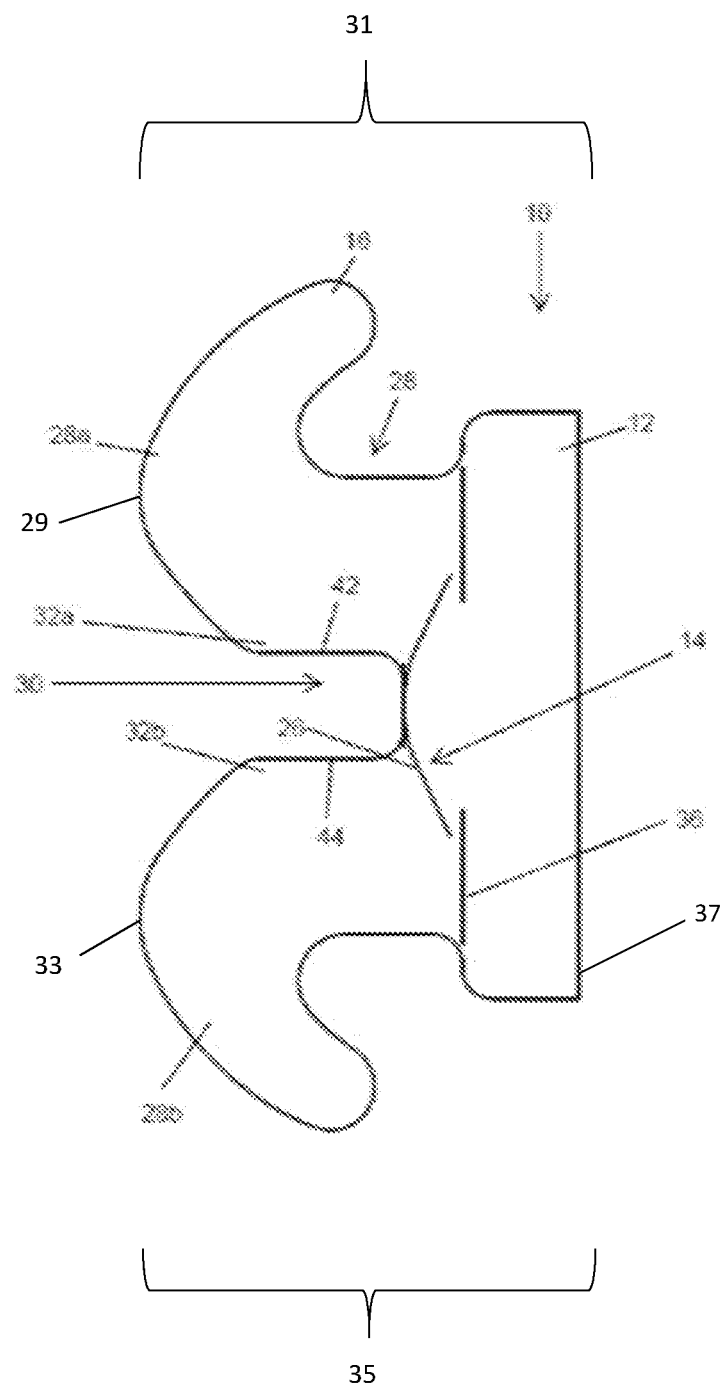
FIG. 3 is a side view of the bracket assembly of FIG. 1, where the opposing side view of the bracket assembly of FIG. 1 is identical.
Figure 4:
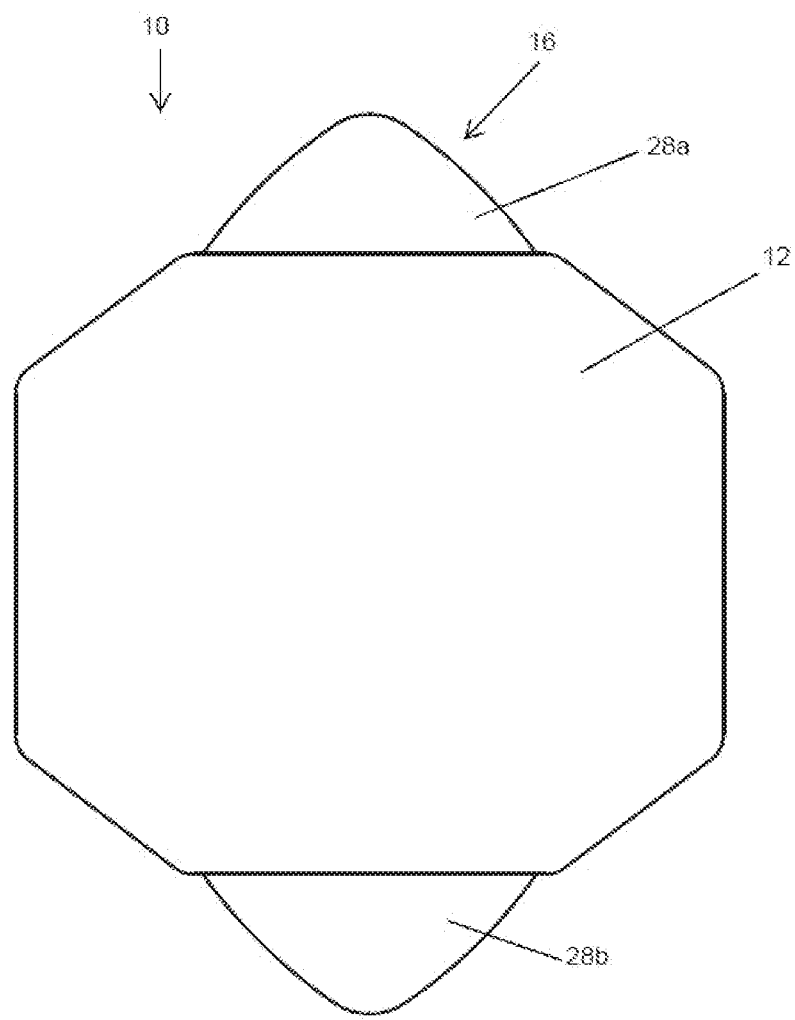
FIG. 4 is a rear view of the bracket assembly of FIG. 1.

Support member 14 may be configured with a generally square body portion 24 coupled with a plurality of tabs 26 extending laterally outward therefrom. More particularly, and as shown in at least FIGS. 2, 3, and 5, tabs 26 project laterally outwardly from body portion 24 and also project in a forward direction (i.e., away from a tooth). In this way, tabs 26 are angled forwardly and outwardly relative to body portion 24. In one embodiment, body portion 24 and tabs 26 may be integrally formed together, however, in alternative embodiments, body portion 24 and tabs 26 may be separable from each other and removably coupled to each other during use of bracket assembly 10. Illustratively, and as shown in FIGS. 2 and 3, a rearward surface 34 of tabs 26 may be flush against a forward surface 36 of mounting plate 12 such that there is no space defined therebetween or separation between rearward surface 34 of tabs 26 and forward surface 36 of mounting plate 12. Body portion 24 and tabs 26 may be configured with any shape applicable to bracket assembly 10.

As with mounting plate 12, support member 14 may be comprised of a ceramic material, although additional embodiments of support member 14 may be comprised of polymeric and/or metallic materials instead of or in addition to a ceramic material. For example, at least illustrative tabs 26 may be comprised of a material configured to bend or flex in response to a pressure applied thereto. More particularly, as orthodontic treatment progresses, wires of increased stiffness are used and, if the interface of the stiff wire and tabs 26 is stiff and unbending, it may be difficult to seat the wire in slot 30. However, in one embodiment, tabs 26 are comprised of a material configured to flex or bend, such as a flexible metal. In this way, tabs 26 may flex when in contact with the stiff wire, thereby providing a force that is felt by the attached tooth. Thus, if using a conventional orthodontic bracket, only the wire has the ability to flex, however, bracket assembly 10 of the present disclosure presents a combination of flexing or bending which is capable by both the wire and tabs 26 for increasing the force applied to the attached tooth. Additionally, the ability for tabs 26 to flex allows for ease of seating the wire within slot 30.

Referring again to FIGS. 1-5, bracket member 16 of bracket assembly 10 may be supported on mounting plate 12 through support member 14. For example, bracket member 16 may be removably or fixedly coupled to support member 14 with conventional couplers, such as mechanical fasteners, adhesives, welds, rivets, or any other type of coupling mechanism. In this way, the position of bracket member 16 may be adjusted relative to support member 14 and mounting plate 12 before bracket member 16 is coupled to support member 14. However, once coupled to support member 14, the position of bracket member 16 may remain fixed. As with mounting plate 12 and support member 14, bracket member 16 may be comprised of a ceramic material, although additional embodiments of bracket member 16 may be comprised of polymeric and/or metallic materials instead of or in addition to a ceramic material.

Bracket member 16 includes a tie-wing 28 having a first portion 28a and a second portion 28b. As such, illustrative bracket member 16 defines a single-tie wing configuration, rather than a double tie-wing configuration which includes at four portions. Illustratively, first portion 28a defines an upper portion of tie-wing 28 extending in a first or upward direction and second portion 28b defines a lower portion of tie-wing 28 extending in a second or downward direction generally opposite the first direction of portion 28a. The upper portion of tie-wing 28 includes an apex 29 having a height 31 from bottom surface 37 of the mounting plate 12. The lower portion of tie-wing 28 includes an apex 33 having a height 35 from the bottom surface 37 of the mounting plate 12. The height 35 is substantially equal to the height 31.

First and second portions 28a, 28b also are configured to project in a forward direction (i.e., away from a tooth) and angle, curve, or bend upwardly or downwardly, respectively. In this way, first and second portions 28a, 28b define hook-type portions of tie-wing 28 which may be configured to receive a coupler 38 (FIG. 1), such as a rubber band or the like, as disclosed further herein. In one embodiment, first and second portions 28a, 28b may be comprised of a material configured to flex or bend when a pressure is applied, thereby facilitating assembly of a rubber band thereon. However, if first and second portions 28a, 28b are comprised of a material configured to flex or bend, the material may be biased toward the position shown in FIGS. 1-5, such that after a rubber band is applied, first and second portions 28a, 28b return to their respective upward and downward positions to maintain tension on the rubber band.

Tie-wing 28 of bracket member 16 also defines a slot 30 positioned intermediate first and second portions 28a, 28b. More particularly, slot 30 is positioned vertically intermediate first and second portions 28a, 28b. Slot 30 is defined by parallel surfaces 42, 44 of first portion 28a and second portion 28b, respectively, of bracket member 16. Slot 30 is configured to receive a wire 40 (FIG. 1) or the like which extends around a portion of the teeth needing adjustment and is positioned within adjacent slots on adjacently-positioned bracket assemblies 10. Slot 30 generally defines a rectangular cross-sectional profile defined by parallel surfaces 42, 44, as shown best in FIGS. 1 and 3, which allows any wire 40 inserted therein to be adjusted in any dimension to apply a force or torque against bracket assembly 10 and the tooth in any number of ways necessary to move the tooth to a desired position.

Figure 1:
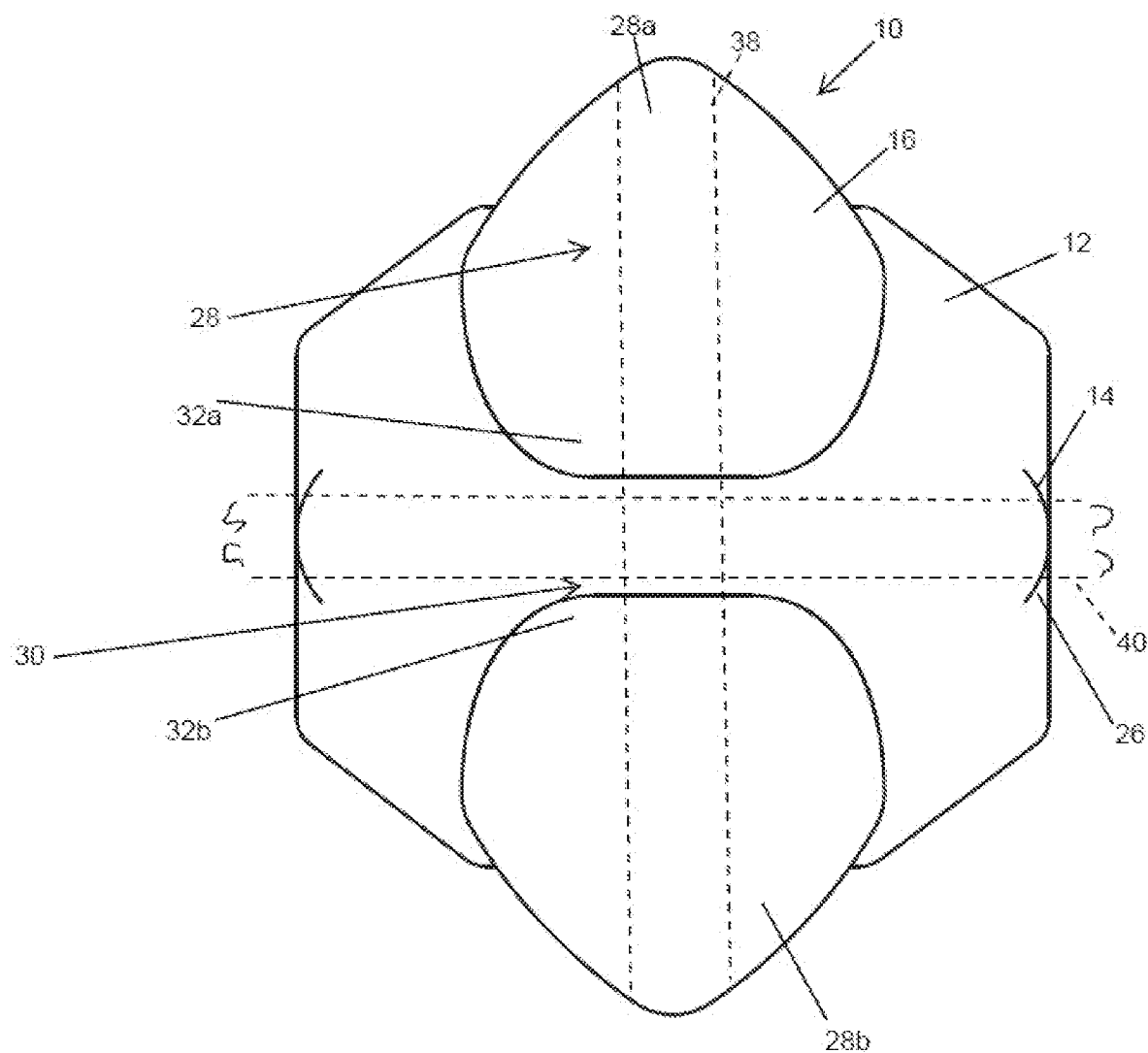
FIG. 1 is a front view of an illustrative orthodontic bracket assembly of the present disclosure, where the bracket assembly is at least partially comprised of a ceramic material.

However, as shown best in FIGS. 1 and 3, slot 30 is configured with a parabolic entrance. More particularly, the outermost extends of parallel surfaces 42, 44 define an entrance of slot 30 which is generally curved, rounded, or acuate. More particularly, the entrance of slot 30 defines a "U" shape due to curved surfaces 32a, 32b of first and second portions 28a, 28b of tie-wing 28, respectively, which extend outwardly from parallel surfaces 42, 44, respectively. The curved or parabolic entrance of slot 30 is defined as the radius bending or curvature connecting the horizontal portion of portions 28a, 28b defined by surfaces 42, 44 and the vertical portion of portions 28a, 28b. In this way, curved surfaces 32a, 32b define the parabolic entrance of slot 30 which allows wire 40 or the like to be guided towards and seated within slot 30 during assembly of wire 40 with bracket assembly 10. For example, as wire 40 is being inserted into slot 30, wire 40 may initially contact a portion of tie-wing 28, rather than directly moving into slot 30; however, the parabolic entrance of slot 30 guides wire 40 into slot 30. Once in slot 30, the depth thereof retains wire 40 therein. Conversely, without curved surfaces 32a, 32b, wire 40 may contact a blunt end of parallel surfaces 42, 44 and cause difficult when inserting wire 40 into slot 30. Additionally, rubber band 38 or the like may be looped or hooked around portions 28a, 28b of tie-wing 28 to extend in a vertical direction to further retain the wire in slot 30. As may be appreciated, rubber band 38 may be stretched between first and second portions 28a, 28b and is positioned on the outside of wire 40 in a forward direction such that rubber band 38 retains wire 40 in slot 30. Rubber band 38 may be stretched by a dental pick or other similar device.

In this way, the embodiment of FIGS. 1-5 discloses that orthodontic bracket assembly 10 may be comprised of a ceramic material and allows for easier insertion of wire 40 into slot 30 of bracket member 16 when applying bracket assembly 10 to a patient's tooth. More particularly, the parabolic entrance of slot 30 facilitates insertion of wire 40 into slot 30 by allowing for wire 40 glide over curved surfaces 32a, 32b as wire 40 is moved toward slot 30. The curvature or parabolic configuration of curved surfaces 32a, 32b guides and directs wire 40 into slot 30 rather than inhibiting direct insertion of wire 40 therein.

Referring now to FIGS. 6-10, an orthodontic bracket assembly 110 is shown which has generally the same components and features as bracket assembly 10 of FIGS. 1-5. Bracket assembly 110 includes a mounting base or plate 112, a support member 114, and a bracket member 116. Mounting plate 112 is configured to be attached a tooth using convention adhesive or bonding materials and processes. In this way, mounting plate 112 remains in a fixed position on the tooth unless removed therefrom and reattached. Mounting plate 112 may be comprised of a metallic material, such as nickel titanium or titanium molybdenum, although additional embodiments of mounting plate 112 may be comprised of polymeric and/or ceramic materials instead of or in addition to a metallic material. In one embodiment, mounting plate 112 may be configured in an octagonal shape, however, mounting plate 112 may be formed in any shape necessary for attaching to the tooth and/or the application of orthodontic treatment. Illustrative mounting plate 112 also includes rounded or curved edges along a perimeter thereof, which may define a reduction in the amount of mounting plate 112 which is visible, thereby improving the aesthetics of bracket assembly 110 on a patient's tooth.

Figure 10:
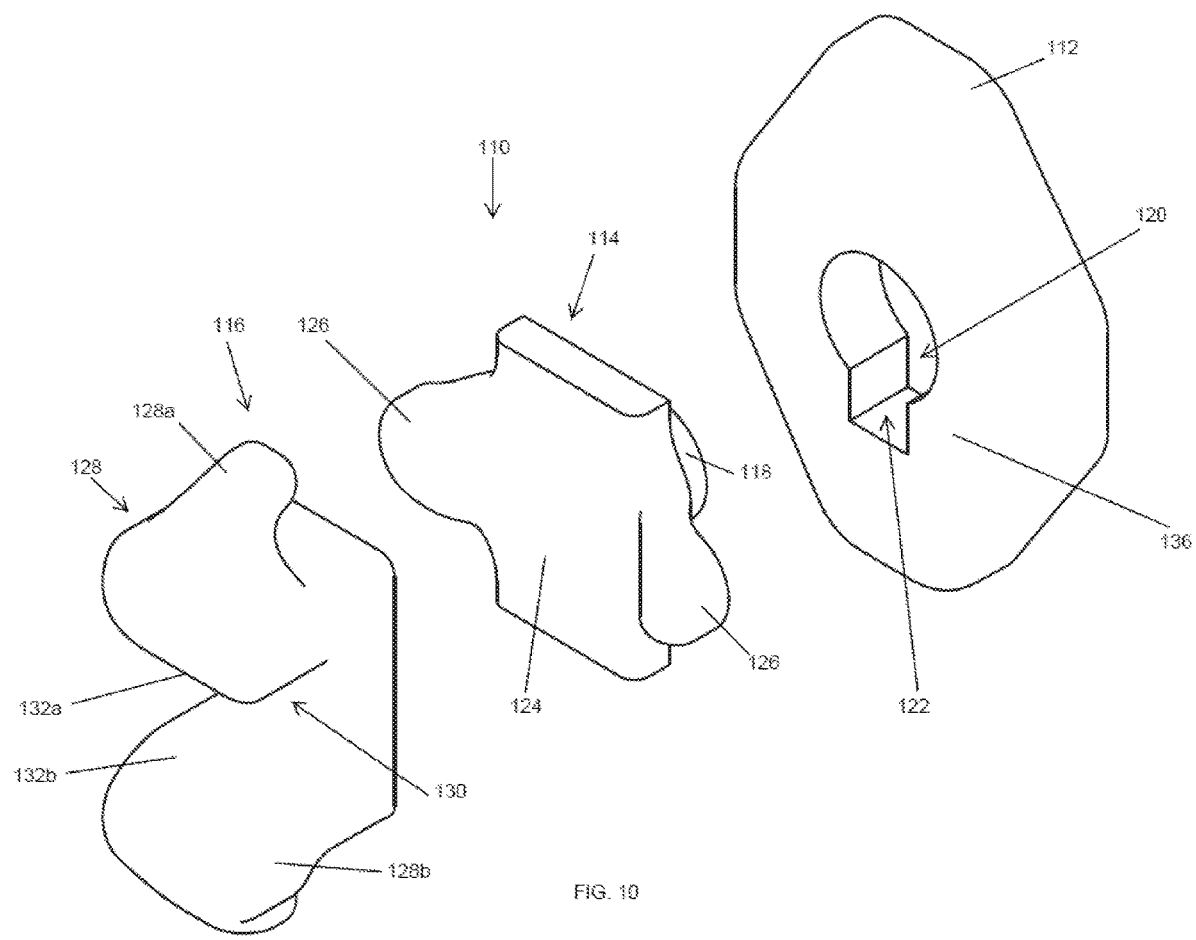
FIG. 10 is an exploded view of the bracket assembly of FIG. 6.

Referring still to FIGS. 6-10, in one embodiment, support member 114 is integrally formed with mounting plate 112, however, as shown in FIG. 10, support member 114 may be removably coupled to mounting plate 112. As shown best in FIG. 10, if support member 114 is configured to be removably coupled to mounting plate 112, support member 114 includes a protrusion 118 extending rearwardy (i.e., towards a tooth) therefrom. Protrusion 118 is configured to be received within an opening 120 of mounting plate 112. When support member 114 is coupled to mounting plate 112, additional coupling members (e.g., mechanical fasteners, adhesive, welds, bonds, or any other type of coupling mechanism) may be used to secure support member 114 to mounting plate 112. Alternatively, protrusion 118 and opening 120 may be configured with a locking feature, such as a key or other projection 119 on protrusion 118 (FIG. 9) configured to be received within a slotted portion 122 of opening 120. Rotational movement or other techniques may be used to then secure support member 114 to mounting plate 112 through key 119 (FIG. 9) on protrusion 118 and opening 120.

Figure 7:
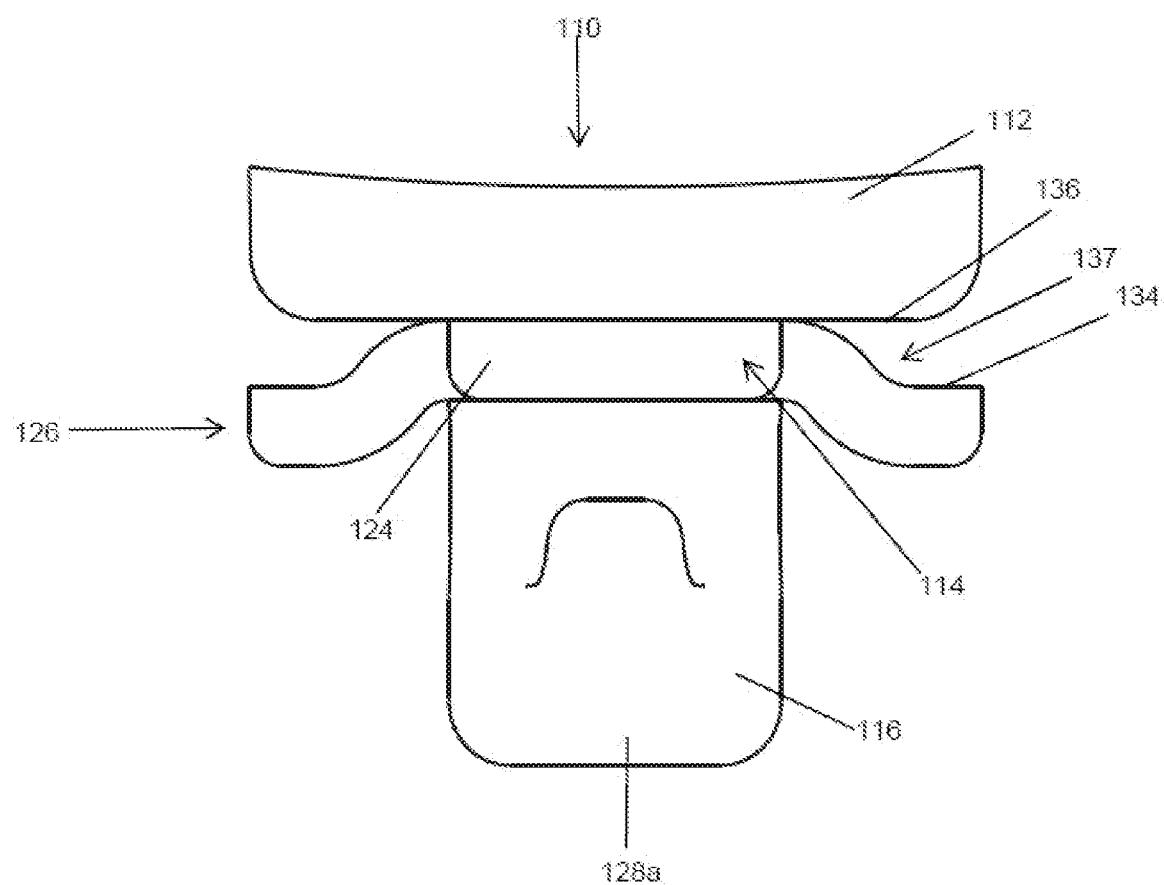
FIG. 7 is a top view of the bracket assembly of FIG. 6, where a bottom view of the bracket assembly of FIG. 6 is identical.
Figure 8:
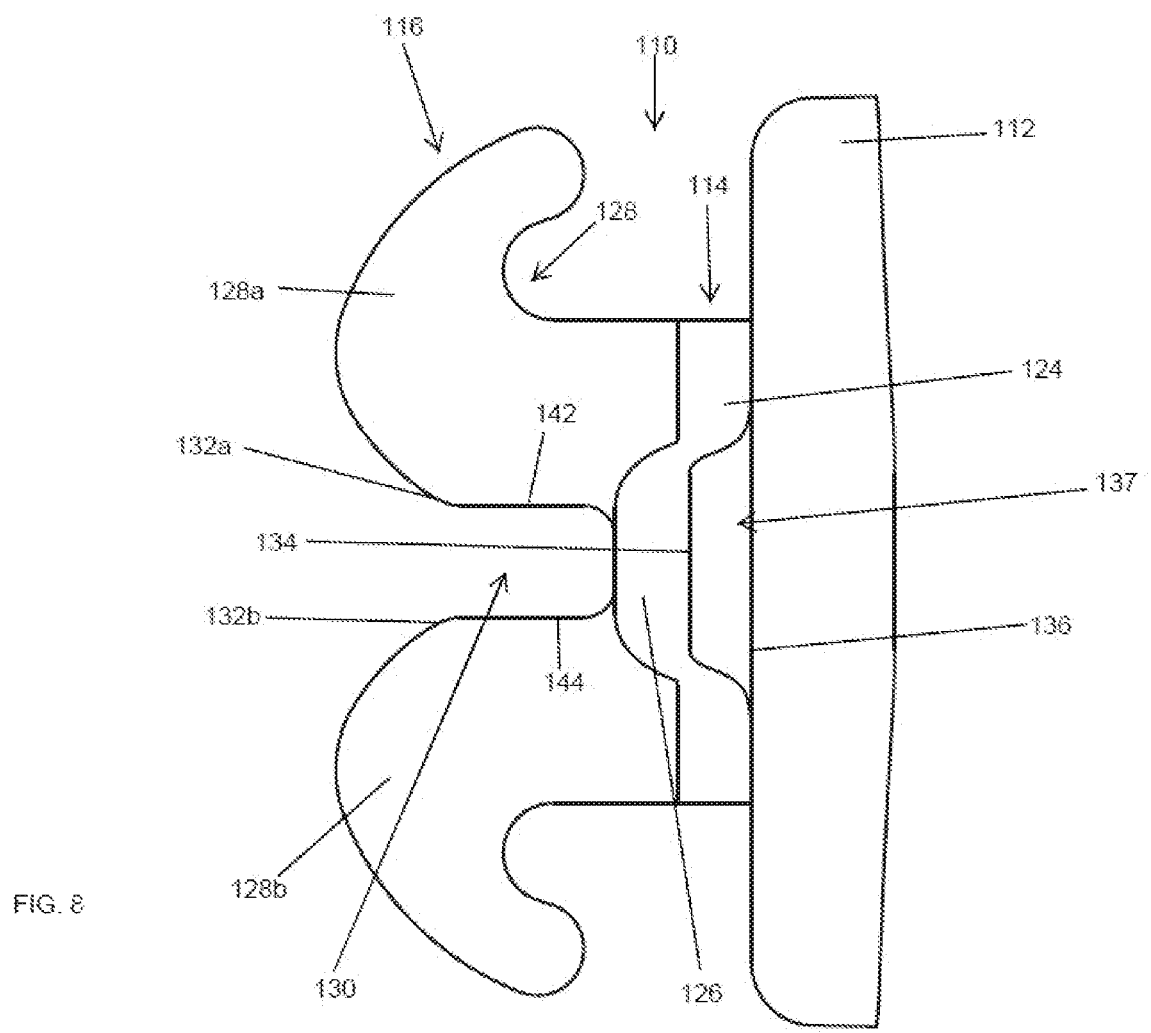
FIG. 8 is a side view of the bracket assembly of FIG. 6, where the opposing side view of the bracket assembly of FIG. 6 is identical.
Figure 9:
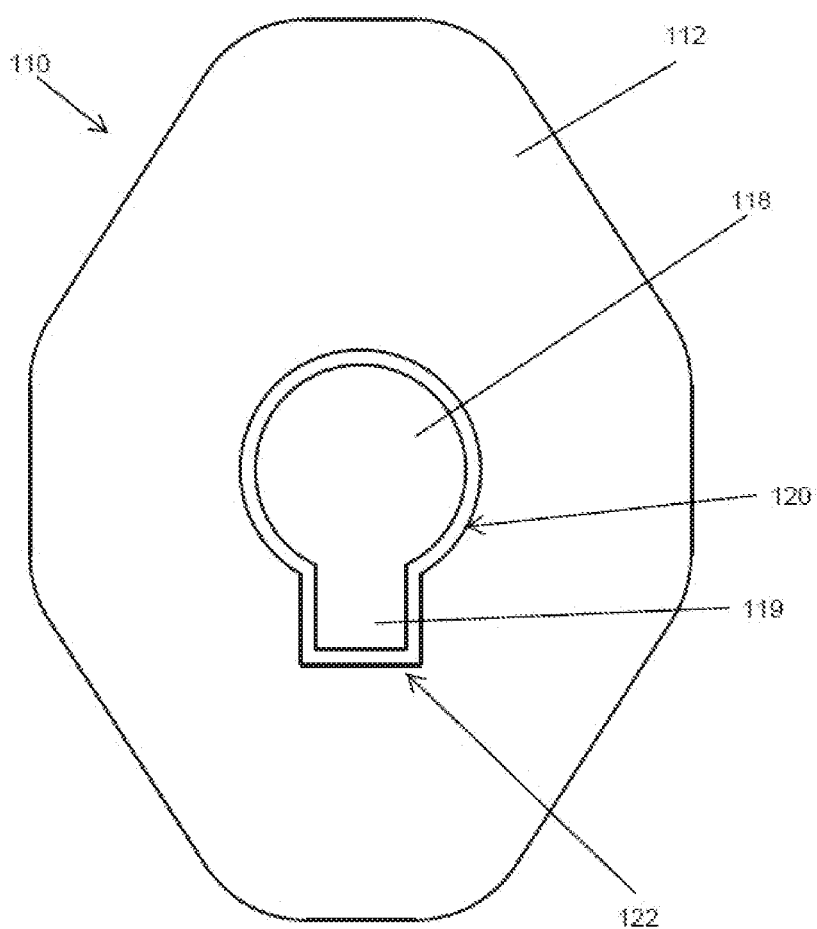
FIG. 9 is a rear view of the bracket assembly of FIG. 6.

Support member 114 may be configured with a generally square body portion 124 coupled with a plurality of tabs 126 extending laterally outward therefrom. More particularly, and as shown in at least FIGS. 7, 8 and 10, tabs 126 project laterally outwardly from body portion 124 and also project in a forward direction (i.e., away from a tooth). In this way, tabs 126 are angled forwardly and outwardly relative to body portion 124. In one embodiment, body portion 124 and tabs 126 may be integrally formed together, however, in alternative embodiments, body portion 124 and tabs 126 may be separable from each other and removably coupled to each other during use of bracket assembly 110. Illustratively, and as shown in FIGS. 7 and 8, a rearward surface 134 of tabs 126 may be spaced apart from a forward surface 136 of mounting plate 112 such that a space or gap 137 may be defined therebetween. Gap 137 may allow for increased flexing or bending of tabs 126 when wire 40 (FIG. 1) is applied thereto, as disclosed herein. However, as shown in FIG. 8, while tabs 126 may be spaced apart from forward surface 136 of mounting plate 112, body portion 124 at least partially contacts forward surface 136 of mounting plate 112. Body portion 124 and tabs 126 may be configured with any shape applicable to bracket assembly 110.

As with mounting plate 112, support member 114 may be comprised of a metallic material, although additional embodiments of support member 114 may be comprised of polymeric and/or ceramic materials instead of or in addition to a metallic material. For example, at least illustrative tabs 126 may be comprised of a material configured to bend or flex in response to a pressure applied thereto. More particularly, as orthodontic treatment progresses, wires, such as wire 40 (FIG. 1), of increased stiffness are used and, if the interface of the stiff wire and tabs 126 is stiff and unbending, it may be difficult to seat the wire in slot 130. However, in one embodiment, tabs 126 are comprised of a material configured to flex or bend, such as a flexible metal. In one embodiment, metallic materials, such as nickel titanium or titanium molybdenum, may have a sufficient modulus of elasticity to allow for such flexibility of tabs 126. In this way, tabs 126 may flex when in contact with the stiff wire, thereby providing a force that is felt by the attached tooth. Thus, while with a conventional orthodontic bracket, only the wire has the ability to flex, bracket assembly 110 of the present disclosure presents a combination of flexing or bending which is capable by both the wire and tabs 126. Additionally, the ability for tabs 126 to flex allows for ease of seating wire 40 within slot 130.

Referring again to FIGS. 6-10, bracket member 116 may be supported on mounting plate 112 through support member 114. For example, bracket member 116 may be removably or fixedly coupled to support member 114 with conventional couplers, such as mechanical fasteners, adhesives, welds, rivets, or any other type of coupling mechanism. In this way, the position of bracket member 116 may be adjusted relative to support member 114 and mounting plate 112 before bracket member 116 is coupled to support member 114. However, once bracket member 116 is coupled to support member 114, the position of bracket member 116 may remain fixed throughout the orthodontic treatment unless bracket assembly 110 is entirely replaced on the tooth. As with mounting plate 112 and support member 114, bracket member 116 may be comprised of a metallic material, although additional embodiments of bracket member 116 may be comprised of polymeric and/or ceramic materials instead of or in addition to a metallic material.

Bracket member 116 includes a tie-wing 128 having a first portion 128a and a second portion 128b. As such, illustrative bracket member 116 defines a single-tie wing configuration. Illustratively, first portion 128a defines an upper portion of tie-wing 128 and second portion 128b defines a lower portion of tie-wing 28. First and second portions 128a, 128b are configured to project in a forward direction (i.e., away from a tooth) and angle, curve, or bend upwardly or downwardly, respectively. In this way, first and second portions 128a, 128b define hook-type portions of tie-wing 128 which may be configured to receive rubber band 38 or the like (FIG. 1), as disclosed further herein. In one embodiment, first and second portions 128a, 128b may be comprised of a material configured to flex or bend when a pressure is applied, thereby facilitating assembly of rubber band 38 thereon. However, if first and second portions 128a, 128b are comprised of a material configured to flex or bend, the material may be biased toward the position shown in FIGS. 6-10, such that after rubber band 38 is applied, first and second portions 128a, 128b return to their respective upward and downward positions to maintain tension on rubber band 38.

Tie-wing 128 of bracket member 116 also defines a slot 130 positioned intermediate first and second portions 128a, 128b. More particularly, slot 130 is positioned vertically intermediate first and second portions 128a, 128b. Slot 130 is defined by parallel surfaces 142, 144 of first portion 128a and second portion 128b, respectively, of bracket member 116. Slot 130 is configured to receive wire 40 (FIG. 1) or the like which extends around a portion of the teeth needing adjustment and is positioned within adjacent slots on adjacently-positioned bracket assemblies 110. Slot 130 generally defines a rectangular cross-sectional profile due to parallel surfaces 142, 144, as shown best in FIGS. 6 and 8, which allows any wire 40 inserted therein to be adjusted in any dimension to apply a force or torque against bracket assembly 110 and the tooth in any number of ways necessary to move the tooth to a desired position.

Figure 6:
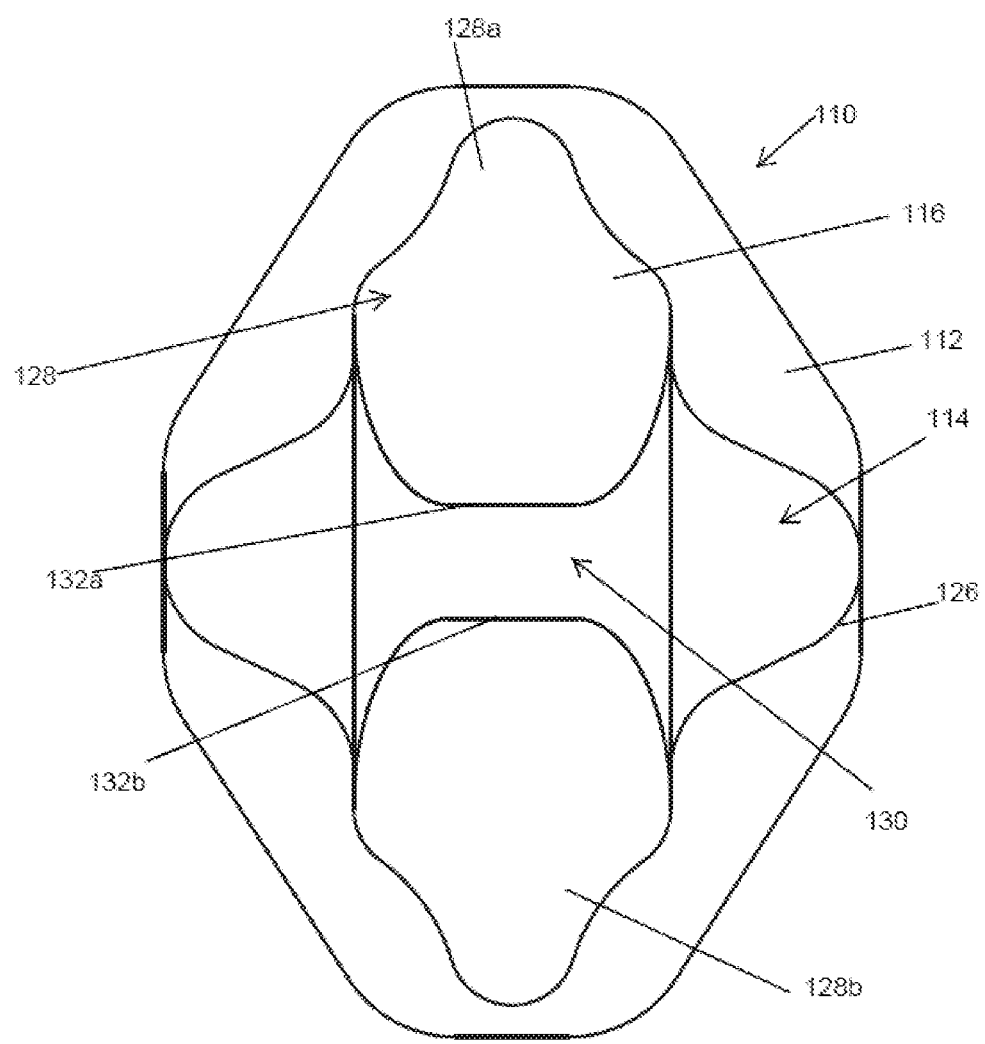
FIG. 6 is a front view of an illustrative orthodontic bracket assembly of the present disclosure, where the bracket assembly is at least partially comprised of a metallic material.

However, as shown best in FIGS. 6 and 8, slot 130 is configured with a parabolic entrance. More particularly, the entrance of slot 130 is generally curved, rounded, or acuate and defines a "U" shape due to curved surfaces 132a, 132b of first and second portions 128a, 128b of tie-wing 128, respectively. The curved or parabolic entrance of slot 130 is defined as the radius bending or curvature connecting the horizontal portion of portions 128a, 128b defined by surfaces 142, 144 and the vertical portion of portions 128a, 128b. In this way, curved surfaces 132a, 132b define the outermost extent of parallel surfaces 142, 144, respectively, and further define the parabolic entrance of slot 130 which allows wire 40 (FIG. 1) or the like to be guided towards and seated within slot 130 during assembly of wire 40 with bracket assembly 110. For example, as wire 40 is being inserted into slot 130, wire 40 may initially contact a portion of tie-wing 128, rather than directly moving into slot 130; however, the parabolic entrance of slot 130 guides wire 40 into slot 130. Once in slot 130, the depth thereof retains wire 40 therein. Additionally, rubber band 38 (FIG. 1) or the like may be looped or hooked around portions 128a, 128b of tie-wing 128 to extend in a vertical direction to further retain wire 40 in slot 130.

In this way, the embodiment of FIGS. 6-10 discloses that orthodontic bracket assembly 110 may be comprised of a metallic material and allows for easier insertion of wire 40 (FIG. 1) into slot 130 of bracket member 116 when applying bracket assembly 110 to a patient's tooth. More particularly, the parabolic entrance of slot 130 facilitates insertion of wire 40 into slot 130 by allowing for wire 40 glide over curved surfaces 132a, 132b as wire 40 is moved toward slot 130. The curvature or parabolic configuration of curved surfaces 132a, 132b guides and directs wire 40 into slot 130 rather than inhibiting direct insertion of wire 40 therein.

Referring now to FIGS. 11-15, an orthodontic bracket assembly 210 is shown and may have some of the same components and features as bracket assembly 10 of FIGS. 1-5 and bracket assembly 110 of FIGS. 6-10. Bracket assembly 210 includes a mounting base or plate 212, a support member 214, and a bracket member 216. Mounting plate 212 is configured to be attached a tooth using conventional adhesive or bonding materials and processes. In this way, mounting plate 212 remains in a fixed position on the tooth unless removed therefrom and reattached. In one embodiment, mounting plate 212 may be configured in a rectangular shape, however, mounting plate 212 may be formed in any shape necessary for attaching to the tooth and/or to comply with the application of the orthodontic treatment. Illustrative mounting plate 212 also includes rounded or curved edges along a perimeter thereof, which may define a reduction in the amount of mounting plate 212 which is visible, thereby improving the aesthetics of bracket assembly 210 on a patient's tooth.

Mounting plate 212 also includes a plurality of detents or projections 213 extending from a forward surface 236 thereof. Illustratively, detents 213 define raised portions of mounting plate 212 and may be arranged in a generally rounded or curved pattern about each lateral side of mounting plate 212. A plurality of grooves 215 may be defined between adjacent detents 213 such that a component of bracket assembly 210 may be positioned within one of grooves 215 and is supported and/or maintained within groove 215 by the adjacent detents 213 defining groove 215, as disclosed further herein. Detents 213 may be equally spaced apart from adjacent detents 213, thereby defining a plurality of equally-sized grooves 215. In one embodiment, grooves 215 are sized to receive a portion of support member 214, as disclosed herein.

Referring still to FIGS. 11-15, support member 214 is configured to be removably coupled to mounting plate 212. Support member 214 includes an opening 221 configured to align with an opening 220 of mounting plate 212. Opening 221 is positioned on a body portion 224 of support member 214. Both openings 221 and 220 of support member 214 and mounting plate 212, respectively, are configured to receive a protrusion 218 (FIG. 14) of bracket member 216, as disclosed further herein. As such, protrusion 218 of bracket member 216 is configured to retain support member 214 on mounting plate 212, however, additional couplers, such as removable mechanical fasteners, may be used to further couple support member 214 with mounting plate 212.

Figure 12:
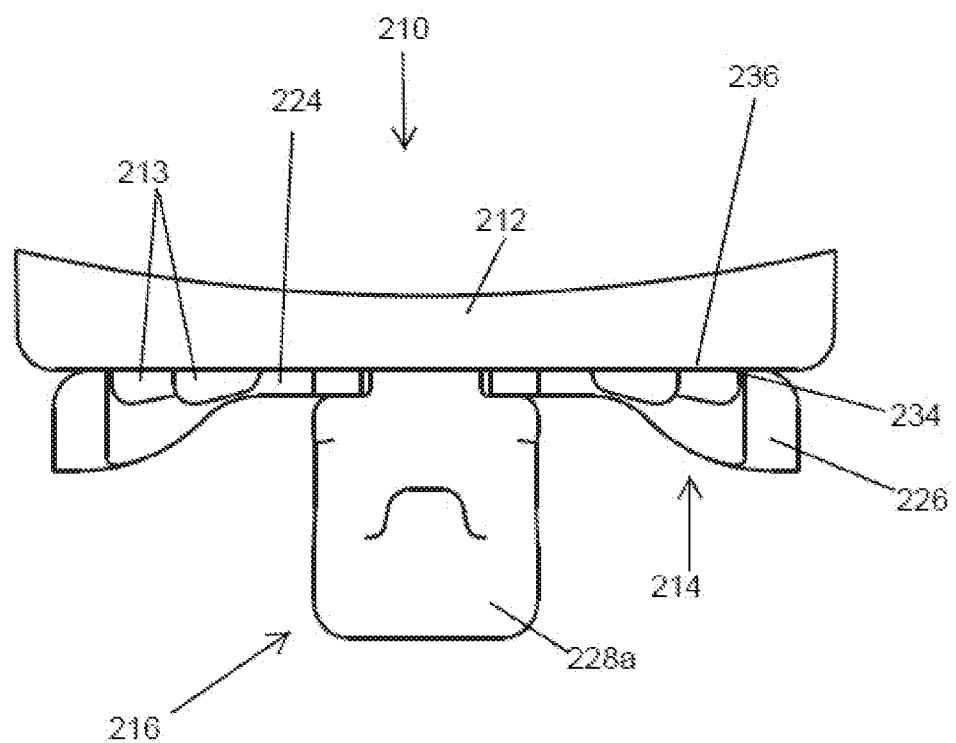
FIG. 12 is a top view of the bracket assembly of FIG. 11, where a bottom view of the bracket assembly of FIG. 11 is identical.
Figure 13:
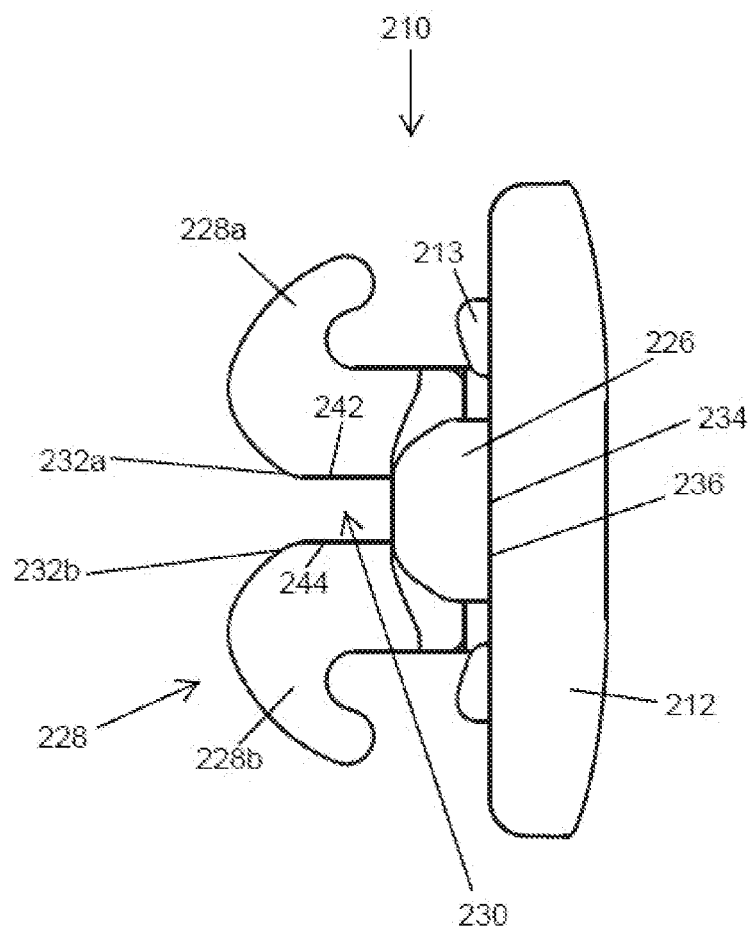
FIG. 13 is a side view of the bracket assembly of FIG. 11, where the opposing side view of the bracket assembly of FIG. 11 is identical.
Figure 14:
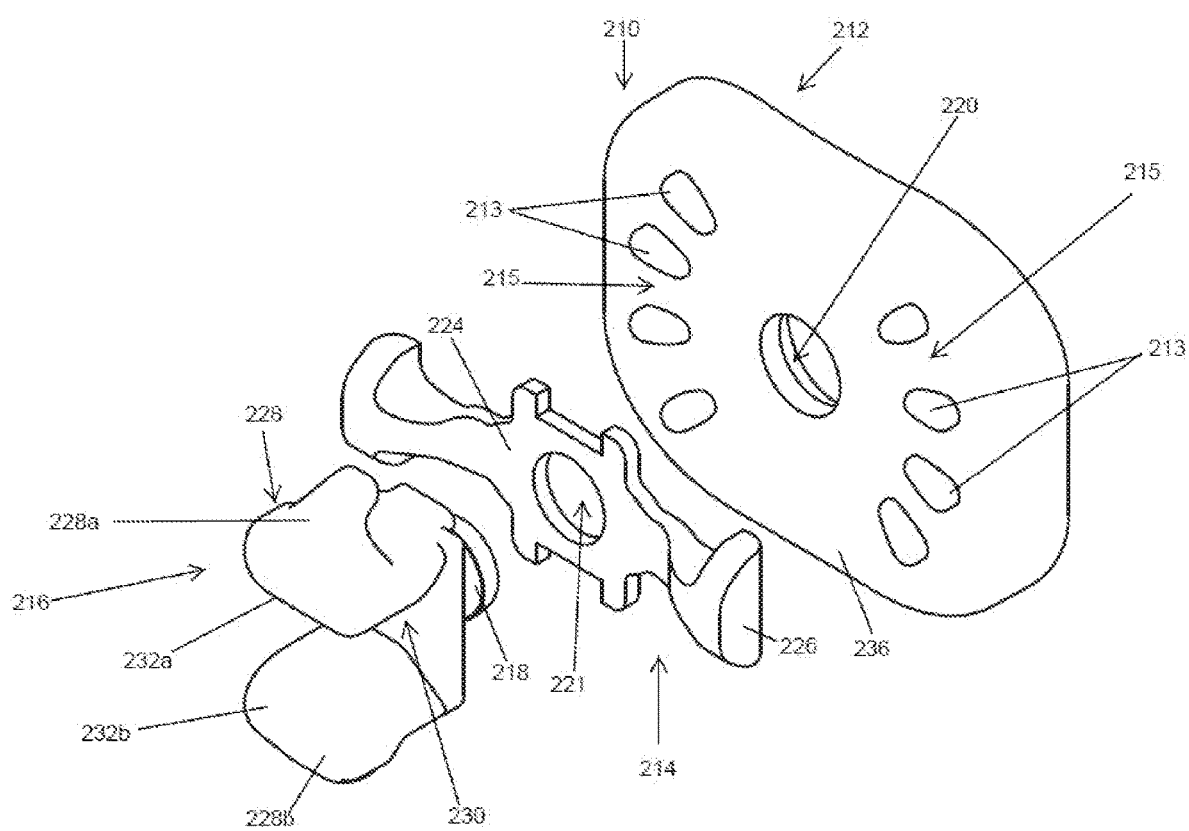
FIG. 14 is an exploded view of the bracket assembly of FIG. 11.
Figure 15:
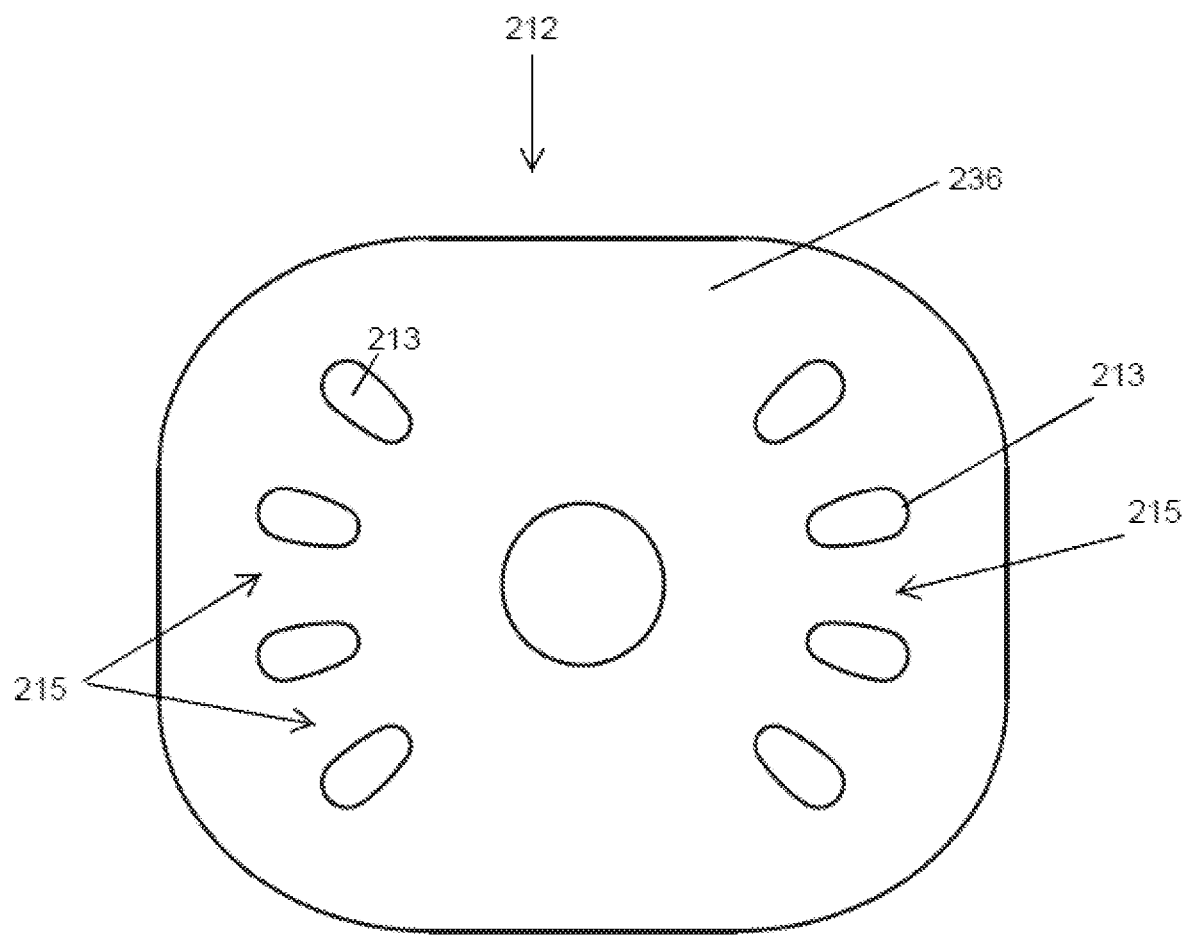
FIG. 15 is a front view of a mounting plate of the bracket assembly of FIG. 11.

Support member 214 may be configured with a generally square body portion 224 coupled with a plurality of tabs 226 extending laterally outward therefrom. More particularly, and as shown in at least FIGS. 12 and 13, tabs 226 project laterally outwardly from body portion 224 and also project in a forward direction (i.e., away from a tooth). In this way, tabs 226 are angled forwardly and outwardly relative to body portion 224. In one embodiment, body portion 224 and tabs 226 may be integrally formed together, however, in alternative embodiments, body portion 224 and tabs 226 may be separable from each other and removably coupled to each other during use of bracket assembly 210. Illustratively, and as shown in FIGS. 12 and 13, a rearward surface 234 of tabs 226 may be flush against forward surface 236 of mounting plate 212 such that there is no space defined therebetween or separation between rearward surface 234 of tabs 226 and forward surface 236 of mounting plate 212. Body portion 224 and tabs 226 may be configured with any shape applicable to bracket assembly 210.

Illustratively, tabs 226 are configured to be received within one of grooves 215 of mounting plate 212. Tabs 226 are retained within groove 215 with adjacent detents 213. Because support member 214 is configured to be removably coupled with mounting plate 212, the position of tabs 226 within any of grooves 215 allows for rotational movement or re-positioning of support member 214 relative to mounting plate 212. Additionally, because bracket member 216 is coupled to support member 214 through protrusion 218 (FIG. 14), rotational movement or re-positioning of support member 214 on mounting plate 212 also causes rotational movement or re-positioning of bracket member 216 relative to mounting plate 212. As such, while bracket assembly 10 of FIGS. 1-5 and bracket assembly 110 of FIGS. 6-10 may allow for the position of bracket member 16, 116 to be adjusted before bracket member 16, 116 and support member 14, 114 are coupled to mounting plate 12, 112, bracket assembly 210 of FIGS. 11-15 allows for continuous adjustment and re-positioning of support member 214 and bracket member 216 relative to mounting plate 212 throughout an orthodontic treatment.

Referring again to FIGS. 11-15, bracket member 216 is configured to couple with support member 214 and mounting plate 212 through protrusion 218 (FIG. 14). Protrusion 218 extends rearwardy (i.e., towards a tooth) from bracket member 216 and is configured to be received within openings 220 and 221 of mounting plate 212 and support member 214, respectively.

Bracket member 216 also includes a tie-wing 228 having a first portion 228a and a second portion 228b, thereby defining a single tie-wing configuration. Illustratively, first portion 228a defines an upper portion of tie-wing 228 and second portion 228b defines a lower portion of tie-wing 228. First and second portions 228a, 228b are configured to project in a forward direction (i.e., away from a tooth) and angle, curve, or bend upwardly or downwardly, respectively. In this way, first and second portions 228a, 228b define hook-type portions of tie-wing 228 which may be configured to receive rubber band 38 (FIG. 1) or the like, as disclosed further herein. In one embodiment, first and second portions 228a, 228b may be comprised of a material configured to flex or bend when a pressure is applied, thereby facilitating assembly of rubber band 38 thereon. However, if first and second portions 228a, 228b are comprised of a material configured to flex or bend, the material may be biased toward the position shown in FIGS. 11-15, such that after rubber band 38 is applied, first and second portions 228a, 228b return to their respective upward and downward positions to maintain tension on rubber band 38.

Tie-wing 228 of bracket member 116 also defines a slot 230 positioned intermediate first and second portions 228a, 228b. More particularly, slot 130 is positioned vertically intermediate first and second portions 228a, 228b. Slot 230 is defined by parallel surfaces 242, 244 of first and second portions 228a, 228b, respectively. Slot 230 is configured to receive wire 40 (FIG. 40) or the like which extends around a portion of the teeth needing adjustment and is positioned within adjacent slots on adjacently-positioned bracket assemblies 210. Slot 230 generally defines a rectangular cross-sectional profile due to parallel surfaces 242, 244, as shown best in FIGS. 11 and 13, which allows any wire 40 inserted therein to be adjusted in any dimension to apply a force or torque against bracket assembly 210 and the tooth in any number of ways necessary to move the tooth to a desired position.

Figure 11:
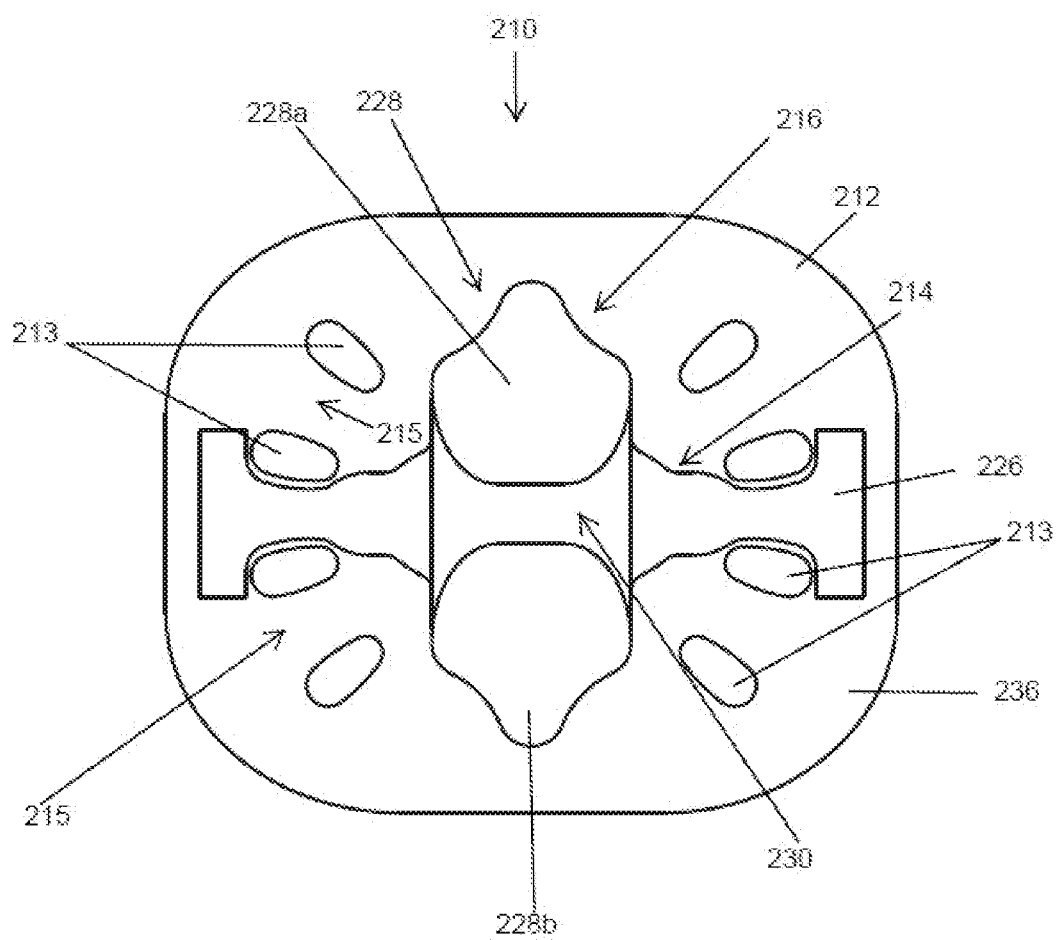
FIG. 11 is a front view of an illustrative orthodontic bracket assembly of the present disclosure, where the bracket assembly is at least partially rotatable.

However, as shown best in FIGS. 11 and 13, slot 230 is configured with a parabolic entrance. More particularly, the entrance of slot 230 is defined by the outermost extents of surfaces 242, 244 and is generally curved, rounded, or acuate. More particularly, the entrance of slot 230 defines a "U" shape due to curved surfaces 232a, 232b of first and second portions 228a, 228b of tie-wing 228, respectively. In this way, curved surfaces 232a, 232b define the parabolic entrance of slot 230 which allows wire 40 (FIG. 1) or the like to be guided towards and seated within slot 230 during assembly of wire 40 with bracket assembly 210. For example, a wire 40 is being inserted into slot 230, wire 40 may initially contact a portion of tie-wing 228, rather than directly moving into slot 230; however, the parabolic entrance of slot 230 guides wire 40 into slot 230. Once in slot 230, the depth thereof retains wire 40 therein. Additionally, rubber band 38 (FIG. 1) or the like may be looped or hooked around portions 228a, 228b of tie-wing 228 to extend in a vertical direction to further retain wire 40 in slot 230.

When bracket assembly 210 is used for on a patient's tooth, mounting plate 212 is adhered or otherwise secured to the tooth. Support member 214 is then joined with mounting plate 212 by positioning tabs 226 of support member 214 within the appropriate grooves 215 on mounting plate 212 to ensure appropriate correction of the patient's tooth. Bracket member 216 then couples with support member 214 and mounting plate 212 by inserting protrusion 218 within openings 221 and 220, respectively. Bracket member 216 also may be secured to support member 214 and/or mounting plate 212 with additional removable couplers (not shown). Once support member 214 and bracket member 216 are located in the desired orientation relative to mounting plate 212, it may be appreciated that slot 230 also is at such an orientation. In this way, the rotational movement or re-positioning of support member 214 on mounting plate 212, through the use of detents 213 and grooves 215, allows for rotational movement or re-positioning of slot 230 of bracket member 216 during the orthodontic process. Wire 40 (FIG. 1) may be inserted into slot 230 when slot 230 is in the desired location and rubber band 38 (FIG. 1) or the like may be positioned outwardly from wire 40 by coupling with first and second portions 228a, 228b of bracket member 216.

In one embodiment, if, during the course of an orthodontic treatment, it is desirable to adjust the location or orientation of slot 230, wire 40 may be removed therefrom and tabs 226 of support member 214 may be flexed or bent outwardly (i.e., away from the tooth) to allow support member 214 and bracket member 216 to rotate within opening 220 of mounting plate 212 before allowing tabs 226 to bias to their unflexed or unbent position to be placed in a different groove 215. As such, it may not be necessary to remove support member 214 or bracket member 216 from mounting plate 212 when adjusting the position or orientation of slot 230.

In this way, bracket assembly 210 is configured to allow slot 230 to rotate between a plurality of discrete positions during the course of an orthodontic treatment. The rotational movement of slot 230 may allow for different angles or locations of force on the tooth using wire 40 inserted therein. Additionally, the ability to move slot 230 between a plurality of discrete positions may allow for a torque to be applied to bracket assembly 210 and/or the tooth and/or allows for any other types of orthodontic adjustments required to move or adjust the tooth to a predetermined position.

While this invention has been described as having exemplary designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

The invention claimed is:

1. An orthodontic bracket assembly, comprising: a mounting plate configured to be coupled to a tooth; and a bracket member including a single tie-wing having a first tie-wing portion generally extending in a first direction, a second tie-wing portion generally extending in a second direction opposite to the first direction, and a slot defined by intermediate planar side walls of the first and second tie-wing portions and configured to receive a wire, and each of the first and second tie-wing portions includes a parabolic surface extending across the respective tie-wing portion and defining an entrance of the slot, wherein the parabolic surface of the first tie-wing portion extends from the respective planar side wall to a first apex having a first height, and the parabolic surface of the second tie-wing portion extends from the respective planar side wall to a second apex having a second height that is substantially the same as the first height.

2. The orthodontic bracket assembly of claim 1, wherein the first direction and the second direction extend perpendicular to the slot.

3. The orthodontic bracket assembly of claim 1, further comprising a support member positioned intermediate the mounting plate and the bracket member.

4. The orthodontic bracket assembly of claim 3, wherein the support member includes a plurality of tabs comprised of a flexible material and configured to contact the wire.

5. The orthodontic bracket assembly of claim 4, wherein a rear surface of the tabs is configured to contact a forward surface of the mounting plate.

6. The orthodontic bracket assembly of claim 4, wherein a rear surface of the tabs is spaced apart from a forward surface of the mounting plate.

7. The orthodontic bracket assembly of claim 3, wherein the support member is removably coupled to the mounting plate and the bracket member is removably coupled to the support member.

8. The orthodontic bracket assembly of claim 1, wherein the slot is configured to move between a plurality of discrete positions.

9. The orthodontic bracket assembly of claim 1, wherein the first and second tie-wing portions are configured to receive a coupler extending between the first and second tie-wing portions and positioned across a portion of the slot.

10. An orthodontic bracket assembly, comprising:
a mounting plate configured to be coupled with a tooth, the mounting plate including an outer surface, a plurality of protrusions extending from the outer surface, and a plurality of grooves positioned between adjacent protrusions;
a support member rotatably coupled to the mounting plate and including a pair of flexible tabs, wherein each tab is configured to be selectively positioned on the outer surface in a groove, and
a bracket member extending from the support member and having a slot configured to receive a wire, and the slot is configured to move between a plurality of discrete angular positions relative to the mounting plate by selectively positioning each of the pair of tabs in opposing grooves.

11. The orthodontic bracket assembly of claim 10, wherein the bracket member includes a first tie-wing portion and a second tie-wing portion positioned on opposing sides of the slot, and each of the first and second tie-wing portions includes a parabolic surface defining an arcuate entrance of the slot.

12. The orthodontic bracket assembly of claim 11, wherein the parabolic surface of the first tie-wing portion extends from a first planar side wall to a first apex having a first height, and the parabolic surface of the second tie-wing portion extends from a second planar side wall to a second apex having a second height that is substantially the same as the first height.

13. The orthodontic bracket assembly of claim 10, wherein the support member rotates relative to the mounting plate without removing the support member from the mounting plate.

14. An orthodontic bracket assembly, comprising:
a mounting plate configured to be coupled to a tooth; and
a bracket member including a single tie-wing having a first tie-wing portion generally extending in a first direction, a second tie-wing portion generally extending in a second direction opposite to the first direction, and a slot defined intermediate planar side walls of the first and second tie-wing portions and configured to receive a wire, and each of the first and second tie-wing portions includes a parabolic surface extending across the respective tie-wing portion defining an entrance of the slot, wherein the parabolic surface of the first tie-wing portion extends from the respective planar side wall to a first apex having a first height, and the parabolic surface of the second tie-wing portion extends from the respective planar side wall to a second apex having a second height that is substantially the same as the first height, and
a support member coupled between the mounting plate and the bracket and including a pair of flexible tabs, the support member being rotatably couple to the mounting plate to rotate the bracket so that the slot moves between a plurality of discrete angular positions relative to the mounting plate by selectively positioning each of the pair of tabs in opposing grooves.

* * * * *